United States Patent [19]

Raju

[11] Patent Number: 4,715,882

[45] Date of Patent: Dec. 29, 1987

[54] SUBSTITUTED PHENOXYPROPIONALDEHYDE DERIVATES AND THEIR USE AS HERBICIDAL AGENTS

[75] Inventor: Muppala S. Raju, Akron, Ohio

[73] Assignee: PPG Industries, Inc., Pittsburgh, Pa.

[21] Appl. No.: 918,955

[22] Filed: Oct. 15, 1986

Related U.S. Application Data

[62] Division of Ser. No. 797,310, Nov. 12, 1986, Pat. No. 4,661,149.

[51] Int. Cl.$^4$ .................. C07C 69/612; C07C 43/205; A01N 57/06; A01N 31/04; A01N 37/34; A01N 37/10

[52] U.S. Cl. .......................................... 71/86; 568/15; 568/49; 568/636; 568/637; 568/638; 71/98; 71/105; 71/100; 71/121; 71/122; 71/123; 71/124; 71/107; 71/115; 71/116; 71/111; 560/255; 558/248; 558/389; 558/396; 558/411; 558/412; 558/243; 558/275; 558/386; 558/387

[58] Field of Search .................. 560/255; 568/15, 49, 568/636, 637, 638; 558/243, 248, 275, 386, 387, 389, 396, 411, 412; 71/86, 98, 105, 100, 121, 122, 123, 124, 107, 115, 116, 111

[56] References Cited

U.S. PATENT DOCUMENTS

| | | | |
|---|---|---|---|
| 4,103,726 | 1/1980 | Matu et al. | 546/157 |
| 4,429,167 | 1/1984 | Lee | 568/636 |
| 4,525,205 | 6/1985 | Lee | 71/94 |

Primary Examiner—Henry R. Jiles
Assistant Examiner—J. Richter
Attorney, Agent, or Firm—Edward J. Whitfield

[57] ABSTRACT

The invention relates to certain substituted phenoxypropionaldehyde derivatives, formulations of said derivatives and the use thereof for preemergence or postemergence control of noxious plants, i.e., weeds.

4 Claims, No Drawings

SUBSTITUTED PHENOXYPROPIONALDEHYDE DERIVATES AND THEIR USE AS HERBICIDAL AGENTS

This is a division of application Ser. No. 797,310, filed Nov. 12, 1985, now U.S. Pat. No. 4,661,149.

FIELD OF THE INVENTION

This invention relates to certain substituted phenoxypropionaldehyde derivatives, formulations of said derivatives and the use thereof for preemergence or postemergence control of noxious plants, i.e., weeds.

DESCRIPTION OF THE INVENTION

This invention provides herbicidally active substituted phenoxypropionaldehyde derivatives represented by the formula:

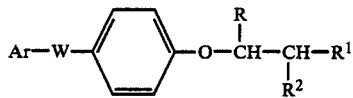

wherein Ar is selected from:

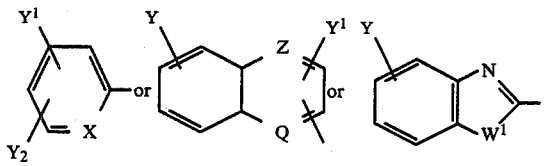

wherein:

W and $W^1$ are independently O, S or NH;
X is CY, N or N or $N\oplus-O\ominus$;
Q is N or $N\oplus-O\ominus$;
Z is CH or N;
Y is hydrogen, halogen, cyano, nitro or lower haloalkyl;
$Y^1$ and $Y^2$ are independently hydrogen, halogen, nitro cyano or lower alkyl, haloalkyl, alkoxy or lower alkoxy;
R is hydrogen or lower alkyl or haloakyl;
$R^1$ is cyano, vinyl, acetynl, dialkylphosphinyl or dialkylphosphonyl; and
$R^2$ is $-OR^3$, $-SR^3$ or $-NR^4R^5$ wherein
$R^3$ is hydrogen, $C_1$ to $C_{10}$ alkyl, cycloalkyl, haloalkyl, hydroxyalkyl, oxoalkyl, alkoxyalkyl, alkenyl, alkynyl, Ar, $-COR^6$ or $-CSR^6$ wherein $R^6$ is $C_1$ to $C_{10}$ alkyl, cycloalkyl, haloalkyl, alkenyl, alkynyl, amino, Ar, $-COOR^7$ or $-COSR^7$ wherein $R^7$ is hydrogen, alkali metal,
$C_1$ to $C_{10}$ alkyl, cycloalkyl, haloakyl, alkenyl, alkynyl or Ar; and
$R^4$ and $R^5$ are independently hydrogen or lower alkyl.

Preferred compounds of the invention are those wherein R is lower alkyl, $R^1$ is cyano and $R^2$ is $-OR^3$.

The compounds of the invention may be prepared using techniques and starting materials known and available to those skilled in the art, and preparation of certain of the invention compounds are illustrated by the following Examples, wherein invention compounds of the following formula are prepared:

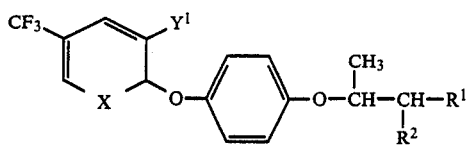

| Example | X | $Y^1$ | $R^1$ | $R^2$ |
|---|---|---|---|---|
| I | CH | —Cl | —CN | —O—COO—$C_2H_5$ |
| II | CH | —Cl | —CN | —O—COCH$_2$Cl |
| III | N | —H | —CN | —O—COO—$C_2H_5$ |
| IV | CH | —Cl | —CN | O—CO—$CH_3$ |
| V | CH | —Cl | —CN | —O—CO—COO—$C_2H_5$ |
| VI | CH | —Cl | —CN | —O—COS—$C_2H_5$ |
| VII | CH | —Cl | —CN | —OCH$_3$ |
| VIII | CH | —Cl | —P=O—(OCH$_3)_2$ | —OH |

EXAMPLE I

Preparation of: 2-ethoxycarbonyloxy-3-[4-(2-chloro-4-trifluoromethylphenoxy) phenoxy]butyronitrile.

To a 100 milliliter flask provided with magnetic stirring bar and a drying tube were charged 0.5 gram of 2-[4-(2-chloro-4-trifluoromethylphenoxy) phenoxy]propionaldehyde, 0.5 gram of sodium cyanide, 0.12 gram of tetrabutyl ammonium hydrogen sulfate, 30 milliliters of methylene chloride and 0.2 milliliter of ethyl chlorocarbonate. After stirring overnight at room temperature, TLC analysis indicated the presence of a considerable amount of unreacted starting material so an additional 0.5 gram of sodium cyanide and 0.2 milliliter of ethyl chlorocarbonate were added and stirring was continued for 2.5 hours after which time an additional 0.2 milliliter of ethyl chlorocarbonate was added. After stirring an additional hour TLC indicated presence of some starting material so 1.0 gram of potassium cyanide and 0.1 gram of 18-crown-6 were added. After stirring at room temperature, an additional 1.5 hours, the reaction mixture was transferred to a separatory funnel, diluted with 150 milliliters of diethyl ether and washed with 4×50 milliliter portions of water. The organic layer was dried and evaporated affording about 1.0 gram of a brown, viscous residue. The residue was dissolved in methylene chloride and eluted over silica gel using methylene chloride as the eluent. The first four 50 milliliter fractions were combined and evaporated affording about 0.6 gram of colorless, gummy material confirmed by PMR analysis as the desired product.

EXAMPLE II

Preparation of: 2-chloroacetateoxy-3-[4-(2-chloro-4-trifluoromethylphenoxy)phenoxy]butylronitrile.

A mixture of 0.3 gram of 2-[4-(2-chloro-4-trifluoromethylphenoxy)phenoxy]propionaldehyde, 0.6 grams of sodium cyanide, 0.06 grams of tetrabutyl ammonium hydrogen sulfate, 0.1 grams of chloroacetyl chloride and 30 milliliters of methylene chloride was stirred at room temperature and under a nitrogen blanket for about 17 hours. Since TLC analysis indicated the presence of substantial unreacted starting material, 1.0 gram of powdered sodium cyanide and 0.1 gram of chloroacetyl chloride were added and stirring continued for 1.5 hours. Since TLC analysis still indicated some unreacted starting material and additional 0.1 gram of chloroacetyl chloride was added and stirring continued for 2 hours at room temperature. The reaction mixture was then diluted with 100 milliliters of diethyl ether and washed consecutively with 2×40 milliliter portions of water, 2×40 milliliter portions of dilute aqueous sodium carbonate and 2×40 milliliter portions of water. The organic phase was dried and evaporated affording about 0.4 gram of colorless, viscous material confirmed by PMR and MS analyses as the desired product.

EXAMPLE III

Preparation of: 2-ethoxycarbonyloxy-3-[4-(5-trifluoromethyl-2-pyridyloxy)phenoxy]butyronitrile.

A mixture of 0.28 grams of 3-[4-(5-trifluromethyl-2-pyridyloxy) phenoxy]propionaldehye, 1.0 gram of powdered sodium cyanide, 0.1 gram of tetrabetyl ammonium hydrogen sulfate, 0.2 milliliter of ethyl chlorocarbonate and 40 milliliters of methylene chloride was stirred overnight at room temperature under a nitrogen blanket. The reaction mixture was then diluted with 50 milliliters of methylene chloride and washed consecutively with 2×40 milliliter portions of water, 2×40 milliliter portions of saturated aqueous sodium bicarbonate and 2×40 milliliter portions of water. The organic phase was dried over anhydrous sodium sulfate and evaporated affording about 0.42 gram of viscous, gummy residue. The residue was eluted over silica gel using methylene chloride as the eluent, 50 milliliter fractions being collected and analyzed by TLC. Fractions 5 through 11 were combined and evaporated affording about 0.3 gram of colorless viscous material confirmed by NMR and MS analyses as the desired product.

EXAMPLE IV

Preparation of: 2-acetyloxy-3-[4-(2-chloro-4-trifluoromethylphenoxy)phenoxy]butyronitrile.

A mixture of 0.5 gram of 2-[4-(2-chloro-4-trifluoromethylphenoxy)phenoxy]propionaldehyde, 1.0 gram of potassium cyanide, 0.2 gram of 18-crown-6 and 40 milliliters of methylene chloride was stirred for one hour at room temperature at which time 0.1 milliliter of acetyl chloride was added, followed by an additional 0.1 milliliter of acetyl chloride about 40 minutes later. After stirring overnight, TLC analysis indicated the presence of trace amounts of unreacted starting material, so two additional 0.1 milliliter portions of acetyl chloride were added and stirring continued, at room temperature, for about a total of 22 hours. The reaction mixture was then evaporated, the residue was taken up in 150 milliliters of diethyl ether and washed with 4×40 milliliter portions of water. The organic phase was dried and evaporated and the resulting viscous residue was eluted over silica gel using a 1:2 V/V mixture of hexane:methylene chloride as the eluent. 50 milliliter fractions of eluent were collected and analyzed by TLC analysis. The fractions containing the desired product were combined and evaporated affording about 0.45 gram of colorless viscous liquid confirmed by spectral analysis as the desired product.

EXAMPLE V

Preparation of: 2-ethyloxalateoxy-3-[4-(2-chloro-4-trifluoromethylphenoxy)phenoxy]butyronitrile.

A mixture of 0.6 gram of 3-[4-(2-chloro-4-trifluoromethylphenoxy)phenoxy]propionaldehyde, 1.2 gram of potassium cyanide, 0.2 gram of 18-crown-6 and 40 milliliters of methylene chloride were stirred at room temperature for one hour at which time 0.3 milliliter of ethyl oxalylchloride was added and stirring was continued overnight. An additional 0.3 milliliter of ethyl oxalylchloride was added and stirring was continued another 4 hours. The reaction mixture was then evaporated, taken up in 150 milliliters of diethyl ether and washed with 4×50 milliliter portions of water. Drying and evaporation afforded about 0.8 gram of viscous liquid residue. The residue was purified over silica gel using methylene chloride as the eluent, 50 milliliter fractions being collected and analyzed by TLC. The fractions containing the desired product were combined and evaporated affording about 0.3 gram of material, confirmed by spectral analysis as the desired product.

EXAMPLE VI

Preparation of: 2-thioethylcarbonyloxy-3-[4-(2-chloro-4-trifluoromethylphenoxy)phenoxy]butyronitrile.

A mixture of 0.6 gram of 2-[4-(2-chloro-4-trifluoromethylphenoxy)phenoxy]propionaldehyde, 0.35 gram of potassium cyanide, 0.2 gram of 18-crown-6 and 30 milliliters of methylene chloride were stirred at room temperature overnight after which time 0.3 milliliter of thioethyl carbonyl chloride was added and stirring was contained another 4 hours. The reaction mixture was then evaporated, the residue was taken up in 20 milliliters of methylene chloride and filtered through silica gel. The filtrate was evaporated affording about 0.6 gram of gummy colorless material shown, by TLC and PMR analyses, to be a mixture containing the desired product. Subsequent purification by adsorption on silica gel, using a 1:1 V/V mixture of hexane:methylene chloride as the eluent, afforded about 0.3 gram of material identified by spectral analysis as the desired product.

EXAMPLE VII

Preparation of: 2-methoxy-3-[4-(2-chloro-4-trifluoromethylPhenoxy)phenoxy]butyronitrile.

A mixture of 0.6 gram of 2-[4-(2-chloro-4-(2-chloro-4-trifluoromethylphenoxy)phenoxy]propionaldehyde, 0.35 gram of potassium cyanide 0.2 gram of 18-crown-6 and 30 milliliters of methylene chloride was stirred at room temperature under a nitrogen blanket for about 5 hours, at which time TLC analysis indicated complete consumption of starting material. One milliliter of methyl iodide and 0.5 gram of potassium carbonate were then added and stirring at room temperature was continued for about 65 hours. TLC analysis indicated the presence of some starting material so an additional 1.0 milliliter of methyl iodide was added and stirring was continued another 24 hours. The reaction mixture was then evaporated, the residue was taken up in 150 milliliters of diethyl ether and washed with 3×30 milliliter portions of water. Solvent was evaporated and the residue was purified by adsorption on silica gel and eluted with 1:1 V/V mixture of hexane:methylene chloride. 50 milliliter fractions being collected and analyzed by TLC. Subsequent combination and evaporation of the appropriate fractions afforded 0.25 gram of material. Since spectral analysis of this material indicated it to be a mixture of compounds, the same was subjected to preparative TLC purification to isolate the desired product.

EXAMPLE VIII

Preparation of: dimethyl-2-hydroxy-3-[4-(2-chloro-4-trifluoromethylphenoxy)phenoxy]propyl phosphonate.

To a stirred mixture of 2.6 grams of 3-[4-(2-chloro-4trifluoromethylphenoxy)phenoxy]propionaldehyde and 0.88 grams of dimethyl phosphite was added 2.9 grams of potassium fluoride. Stirring was stopped and the mixture solidified in about 10 minutes. After standing for about 2 hours, the solidified reaction mixture was taken up in 50 milliliters of methylene chloride and filtered. The filtrate was evaporated affording a viscous, colorless residue. The residue was adsorbed on silica gel and eluted with methylene chloride and ethyl acetate. Evaporation of the ethyl acetate fractions afforded about 3.0 grams of material identified by spectral analysis as the desired product.

EXAMPLES IX to XII

Following the procedures described in the foregoing Examples but using 3-[4-(5-trifluoromethyl-2-pyridyloxy)phenoxy]-2-hydroxy butyronitrile (prepared in situ in Example III) as a starting material, the following compounds were also prepared:

IX. The compound, 2-phenoxycarbonyl-3-[4-(5-trifluoromethyl-2-pyridyloxy)phenoxy]butyronitrile, by reaction of said starting material with phenyl chloroformate.

X. The compound, 2-acetyloxy-3-[4-(5-trifluoromethyl-2pyridyloxy)phenoxy]butyronitrile, by reaction of said starting material with acetylchloride.

XI. The compound, 2-methyloxycarbonyloxy-3-[4-(5-trifluoromethyl-2-pyridyloxy)phenoxy]butyronitrile, by reaction of said starting material with methylchloroformate.

XII. The compound, 2-allyloxycarbonyloxy-3-[4-(5-trifluormethyl-2-pyridyloxy)phenoxy]butyronitrile, by reaction of said starting material with allyl chloroformate.

Although the invention has been illustrated by the foregoing Examples with regard to the preparation of certain compounds within the scope of the invention, it is to be understood that other compounds within the scope of the invention may readily be prepared by those skilled in the art simply by varying the choice of starting materials and using the same or similar techniques.

Weed control in accordance with this invention is effected by applying to the soil prior to emergence of weeds therefrom or to the plant surfaces subsequent to emergence from the soil, a herbicidally effective amount of a compound of this invention. It is, of course, to be understood that the term "a compound of this invention" also includes mixtures of such compounds or a formulation containing a compound or mixture of compounds of this invention.

The term "herbicidally effective amount" is that amount of a compound of this invention required to so injure or damage weeds such that the weeds are incapable of recovering following application while not causing substantial injury to any valuable crop amongst which the weeds might be growing. The quantity of a compound of this invention applied in order to exhibit a satisfactory herbicidal effect may vary over a wide range and depends on a variety of factors, such as, for example, hardiness of a particular weed species, extent of weed infestation, climatic conditions, soil conditions, method of application, and the like. Typically, one or less pound per acre of a compound of this invention would be expected to provide satisfactory weed control, although in some instances application rates in excess of one pound per acre, e.g., up to 2 or more pounds per acre might be required. Of course, the efficacy of a particular compound against a particular weed species may readily be determined by routine laboratory or field testing in a manner well known to the art. It is expected that satisfactory weed control can be had at a rate of application in the range of 0.1 to 1.0 pound per acre.

Of course, a compound of this invention can be formulated according to routine methods with any of several known and commonly used herbicidal diluents, adjuvants and carriers. The formulations can contain liquid carriers and adjuvants such as organic solvents, as well as emulsifiers, stabilizers, dispersants, suspending agents, spreaders, penetrants, wetting agents and the like. Typical carriers utilized in dry formulations include clay, talc, diatomaceous earth, silica and the like. Preferred formulations are those in the form of wettable powders, flowables, dispersible granulates or aqueous emulsifiable concentrates which can be diluted with water at the site of application. Also, dry formulations such as granules, dusts, and the like, may be used.

When desired, a compound of this invention can be applied in combination with other herbicidal agents in an effort to achieve even broader vegetative control. Typical herbicides which can be conveniently combined with Formula I compound include atrazine, hexazinone, metribuzin, ametryn, cyanazine, cyprazine, prometon, prometryn, propazine, simazine, terbutryn, propham, alachlor, acifluorfen, bentazon, metolachlor and N,N-dialkyl thiocarbamates such as EPTC, butylate or vernolate. These, as well as other herbicides described, for example, in the *Herbicide Handbook of the Weed Science Society of America,* may be used in combination with a compound or compounds of the invention. Typically such formulations will contain from about 5 to about 95 percent by weight of a compound of this invention.

The herbicidal formulations contemplated herein can be applied by any of several methods known to the art. Generally, the formulation will be applied as an aqueous spray. Such application can be carried out by conventional ground equipment, or if desired, the sprays can be aerially applied. Soil incorporation of such surface applied herbicides is accomplished by natural leaching, and is of course facilitated by natural rainfall and melting snow. If desired, however, the herbicides can be incorporated into the soil by conventional tillage means.

Compounds of this invention have been found especially useful for controlling grassy weeds but could be used for preemergence and postemergence control of a wide variety of grassy weeds. Typical of the various species of vegetative growth that may be controlled, combated, or eliminated are, for example, annuals such as foxtail, crabgrass, field pennycress, ryegrass, goose grass, wild oats, barnyardgrass, hemp nettle, spurge, pondweed, cheatgrass, fall panicum, witchgrass, watergrass, and similar annual grasses and weeds. Biennials that may be controlled include wild barley, campion, and the like. Also controlled by the compounds of this invention may be perennials such as quackgrass, Johnsongrass, horsetail, cattail, and the like.

The compounds prepared as described in the Examples were individually tested for herbicidal efficacy, against a variety of grassy weed species, under controlled laboratory conditions of light, humidity and temperature. A solvent solution of each compound was applied, both preemergence and postemergence, to test flats containing the various weed species, and herbicidal efficacy was determined by periodic visual inspection, after application of the compounds vis a vis an untreated control. Herbicidal efficacy was determined on a Numerical Injury Rating (NIR) scale of from 0 (no injury) to 10 (all plants dead). A NIR rating of 7–9 indicates severe injury; a NIR rating of 4–6 indicates moderate injury, i.e., plant growth is reduced to the extent that normal growth could be expected, but only under ideal conditions; and a NIR rating of 1–3 indicates slight injury.

The following tables gives the individual and average preemergence (Table I) and postemergence (Table II) NIR determined for the compounds prepared as described in Examples I to VIII on the grassy (GR) weed species to which the compounds were applied, at the indicated rate of application in pounds per acre. The NIR was determined three weeks subsequent to application.

TABLE I

| Compd: | I | II | III | IV | V | VI | VII | VIII |
|---|---|---|---|---|---|---|---|---|
| YLFX | 10 | 7 | 10 | 10 | 9 | 9 | 9 | 9 |
| CBGS | 10 | 7 | 10 | 10 | 10 | 9 | 9 | 10 |
| JNGS | 10 | 7 | 10 | 10 | 9 | 9 | 4 | 8 |
| WOAT | 8 | 5 | 3 | 7 | 7 | 8 | 4 | 5 |
| BNGS | — | 8 | 10 | 8 | 10 | 8 | 3 | 8 |
| Rate | 1.0 | 1.0 | 0.5 | 0.9 | 1.0 | 1.0 | 0.64 | 2.0 |
| Average | 9.5 | 6.8 | 8.6 | 9.0 | 9.0 | 8.6 | 5.8 | 8.0 |

TABLE II

| Compd: | I | II | III | IV | V | VII |
|---|---|---|---|---|---|---|
| YLFX | 10 | 7 | 8 | 7 | 4 | 10 |
| JNGS | 8 | 7 | 7 | 7 | 6 | 10 |
| WOAT | 7 | 7 | 1 | 6 | 1 | 6 |
| BNGS | 10 | — | 9 | — | 10 | 10 |
| Rate | 5.0 | 1.0 | 1.1 | 5.0 | 1.0 | 0.64 |
| Average | 8.8 | 7.0 | 6.3 | 6.7 | 5.3 | 9.0 |

The grassy weeds used in the screening test were barnyardgrass (BNGS), large crabgrass (CBGS), Johnsongrass (JNGS), wild oats (WOAT) and yellow foxtail (YLFX).

Although the invention has been described in considerable detail by the foregoing, it is to be understood that many variations may be made therein by those skilled in the art without departing from the spirit and scope thereof as defined by the appended claims.

I claim:

1. A compound of the Formula:

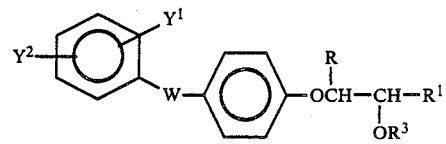

wherein
$Y^1$ and $Y^2$ are independently hydrogen, halogen, nitro, cyano, or lower alkyl, haloalkyl or alkoxy;
W is oxygen or sulfur;
R is hydrogen or lower alkyl or alkoxy;
$R^1$ is cyano, vinyl, acetynyl, lower dialkylphosphinyl or dialkylphosphonyl;
$R^3$ is hydrogen, or up to $C_{10}$ alkyl, cycloalkyl, haloalkyl, hydroxyalkyl, oxoalkyl, alkoxyalkyl, alkenyl, alkynyl or —$COR^6$ or —$CSR^6$ wherein $R^6$ is up to $C_{10}$ alkyl, cycloalkyl, haloalkyl, alkoxy, alkenyl, alkynyl, amino, —$COOR^7$ or —$COSR^7$ wherein $R^7$ is hydrogen, alkali metal, up to $C_{10}$ alkyl, cycloalkyl, haloalkyl, alkenyl or alkynyl.

2. A compound of claim 1 of the Formula

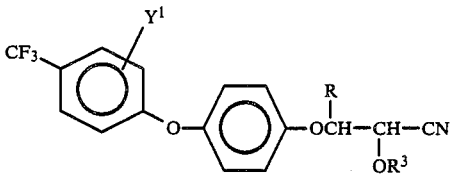

wherein
$Y^1$ is hydrogen or halogen;
R is lower alkyl; and
$R^3$ is hydrogen, up to $C_{10}$ alkyl or haloalkyl or —$COR^6$ or —$CSR^6$ wherein $R^6$ is up to $C_{10}$ alkyl or alkoxy or —$COOR^7$ or —$COSR^7$ wherein $R^7$ is hydrogen alkali metal or up to $C_{10}$ alkyl.

3. A herbicidal composition containing an agronomically acceptable carrier and a herbicidally effective amount of a compound or mixture of compounds defined in claim 1.

4. In a method of controlling weeds wherein a herbically effective amount of herbicide is applied to a growth medium prior to emergence of weeds therefrom or to the weeds subsequent to emergence from the growth medium, the improvment residing in using as the herbicide a compound or mixture of compounds as defined in claim 1.

* * * * *